United States Patent [19]
Weerasooriya et al.

[11] Patent Number: 5,488,148
[45] Date of Patent: Jan. 30, 1996

[54] PROCESS FOR SULFONATING INTERNAL OLEFINS

[75] Inventors: Upali Weerasooriya, Austin; John Lin, Cedar Park; K. Lee Matheson, Austin; Donald T. Robertson, Austin; Janet L. Watson, Austin; LeAnn M. Rowe, Pflugerville, all of Tex.

[73] Assignee: Vista Chemical Company, Houston, Tex.

[21] Appl. No.: 115,313

[22] Filed: Sep. 1, 1993

[51] Int. Cl.$^6$ .................................... C07C 309/20
[52] U.S. Cl. ............................................ 562/123
[58] Field of Search ............................... 562/123

[56] References Cited

U.S. PATENT DOCUMENTS

| | | |
|---|---|---|
| 4,183,867 | 1/1980 | Sekiguchi et al. . |
| 4,248,793 | 2/1981 | Sekiguchi et al. ............. 562/123 |
| 4,925,976 | 5/1990 | Terao et al. ..................... 562/123 |

FOREIGN PATENT DOCUMENTS

| | | |
|---|---|---|
| 0446971 | 9/1991 | European Pat. Off. . |
| 2236538 | 4/1991 | United Kingdom . |

OTHER PUBLICATIONS

H. Yoshimura, et al.: "NMR Study on Sulfonation of Internal Olefins," *JAOCS*, vol. 68, No. 8 (Aug. 1991), pp. 623–628.

J. Stapersma, et al.: "Hydroxy Alkane Sulfonate (HAS), a New Surfactant Based on Olefins," *JAOCS*, vol. 69, No. 1 (Jan. 1992), pp. 39–43.

D. W. Roberts, et al.: "Sulfonation of Internal Olefins," *Commun. Jorn. Com. Esp. Deterg.*, vol. 22, 1991, pp. 21–35.

P. Radici, et al.: "Internal n-Olefin Sulfonates (IOS)—New Insights into the Product," *Commun. Jorn. Com. Esp. Deterg.*, vol. 23, 1992, pp. 205–218.

D. W. Roberts, et al.: "Why Internal Olefins are Difficult to Sulphonate," *Tenside Detergents* 22, No. 4 (1985), pp. 193–195.

*Primary Examiner*—José G. Dees
*Assistant Examiner*—Joseph M. Conrad, III
*Attorney, Agent, or Firm*—Browning, Bushman, Anderson & Brookhart

[57] ABSTRACT

A process for sulfonating internal olefins wherein a dilute solution of the internal olefins in an inert hydrocarbon solvent is sulfonated to produce a reaction mixture containing intermediate sulfonated compounds, the intermediate sulfonated compounds in the reaction mixture being neutralized under conditions to form neutralized sulfonated compounds, the neutralized sulfonated compounds in the reaction mixture being hydrolyzed to form a product mixture containing hydroxy alkane sulfonates and alkene sulfonates that are then recovered.

9 Claims, No Drawings

PROCESS FOR SULFONATING INTERNAL OLEFINS

BACKGROUND OF THE INVENTION

1. Field of the Invention

The present invention relates to a process for producing sulfonated detergent-range internal olefins.

2. Description of the Prior Art

It is well known that alpha olefins can be sulfonated to produce anionic surfactants that are widely used. However, the sulfonation of internal olefins to produce surfactants has not met with commercial success because of the poor quality of the sulfonated internal olefins obtained and the poor yields. Heretofore, sulfonation of internal olefins has been conducted via the sulfonation of mixtures of alpha olefins and internal olefins, neat internal olefins or internal olefins in chlorinated solvents. Recently, internal olefins have been sulfonated under conditions to produce products that are rich in hydroxy alkane sulfonates with low levels of residual sultones, inorganic sulfates and free oil. In an article by J. Stapersma, H. H. Deuling and R. Van Ginkel entitled, "Hydroxy Alkane Sulfonate (HAS), a New Surfactant Based on Olefins" (*JAOCS*, Vol. 69, No. 1, January, 1992, pp. 39–43), there is described the production of hydroxy alkane sulfonates from internal olefins using a falling film glass reactor under mild conditions. Using this technique, it is possible to obtain a product that is rich in hydroxy alkane sulfonates.

SUMMARY OF THE INVENTION

It is therefore an object of the present invention to provide an improved process for the production of sulfonated internal olefins.

Another object of the present invention is to provide a process for the production of hydroxy alkane sulfonates and alkene sulfonates in high yields and with relatively low levels of residual sultones.

Still a further object of the present invention is to provide a process for the production of hydroxy alkane sulfonates and alkene sulfonates that makes use of a relatively inexpensive feedstock as the source of the internal olefins.

The above and other objects of the present invention will become apparent from the description given herein and the appended claims.

According to the process of the present invention, a solution of the internal olefins in an inert hydrocarbon solvent is sulfonated under suitable sulfonation conditions, the internal olefins being present in the hydrocarbon solvent in an amount of from about 5 to about 40% by weight. The sulfonation of the internal olefins produces a mixture of intermediate sulfonated compounds that is neutralized and hydrolyzed under conditions to form a product rich in hydroxy alkane sulfonates and alkene sulfonates that is recovered.

DESCRIPTION OF THE PREFERRED EMBODIMENTS

The internal olefins that can be sulfonated according to the process of the present invention have the general formula:

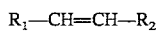

wherein $R_1$ and $R_2$ may be the same or different and are each an alkyl hydrocarbon group containing from about 1 to about 30 carbon atoms. In particular, $R_1$ and $R_2$ are alkyl groups, each of which contains from about 4 to about 15 carbon atoms.

The hydrocarbon solvent that is used in the process of the present invention, in general, can be any hydrocarbon or mixture thereof that is generally inert under sulfonation conditions in the sense that the components of the hydrocarbon solvent do not substantially sulfonate. Additionally, the hydrocarbon solvent must be one that does not deleteriously affect the sulfonation of the internal olefins. The hydrocarbon solvent will be of a composition such that it is liquid at sulfonation conditions. It is contemplated, for example, that the hydrocarbon solvent can comprise a mixture of paraffins, some of which are liquid at sulfonation temperature and some of which are solid at the sulfonation temperature, the mixture being, however, a homogeneous solution at sulfonation conditions. A typical hydrocarbon solvent can comprise a mixture of paraffins in the $C_6$ to $C_{16}$ range, preferably in the $C_{12}$ to $C_{16}$ range.

While the solution of internal olefins and hydrocarbon solvent can be formed by mixing, in suitable proportions, one or more internal olefins with a hydrocarbon, e.g., paraffinic, solvent, it is a feature of the present invention that readily available feedstocks comprised of minor amounts of internal olefins in paraffins are readily available from several sources. For example, in the PACOL® process, marketed by UOP, an essentially paraffinic stream containing paraffins in the range of $C_{12}$ to $C_{16}$ can be dehydrogenated to produce a product stream containing about 10% internal olefins in admixture with about 90% paraffins. Such a stream provides an ideal solution of internal olefins in an inert hydrocarbon solvent to be sulfonated according to the process of the present invention. In general, the internal olefin will be present in the hydrocarbon solvent in an amount of from about 5 to about 40% by weight, more particularly from about 8 to about 15% by weight. With respect to the use of readily available starting material solutions such as PACOL® streams, the process of the present invention obviates the necessity of having to separate internal olefins from other components for carrying sulfonation out on neat internal olefins or for synthetically blending solutions of internal olefins and other, more expensive solvents, as, for example, halogenated hydrocarbons.

The sulfonation of internal olefins, like that of alpha-olefins, proceeds in essentially three steps: sulfonation, neutralization and hydrolysis. Procedures for the sulfonation of internal olefins are well known and documented in the prior art. Procedures for sulfonating internal olefins are disclosed, for example, in the following references:

European Patent Application No. 0446971A 1;

Cavalli, et al. Comun. Jorn. Com. Esp. Deterg., 23, 1992, pp. 205–218; and

Roberts, et al. Comun. Jorn. Com. Esp. Deterg., 22, 1991, pp. 21–35. For example, European Patent Application No. 0 446 971 A1 discloses that internal olefins having from 8 to 26 carbon atoms can be sulfonated in a falling film reactor with a sulfonating agent in a mol ratio of sulfonating agent to internal olefin of 1:1 to 1.25:1 while cooling the reactor with a cooling means having a temperature not exceeding 35° C. and then neutralizing and hydrolyzing the reaction product from the sulfonating step. The sulfonation of the internal olefins is preferably carried out with sulfur trioxide. The cooling means is preferably water having a temperature not exceeding 35° C., more preferably in the range of from about 0° C. to 25° C. The sulfonation may be carried out batchwise, semi-continuously or continuously. The reaction is preferably performed in the falling film reactor, which is cooled by flowing the cooling water at the outside walls of the reactor. At the inner walls of the reactor, the internal olefin flows in a downward direction. $SO_3$ is diluted with nitrogen, air or any other gas, inert under the reaction conditions.

The Cavalli et al. reference teaches that internal olefins can be sulfonated by reacting the olefin and $SO_3$, aging, neutralizing the product with sodium hydroxide and then hydrolyzing. Specifically, the Cavalli reference discloses that sulfonation can occur with an $SO_3$/olefin mol ratio of 1.025, an $SO_3$/air, % of 2.5, an olefin flow rate, kg/h of 14.5, and a cooling jacket temperature, °C. of 8–10. As per the Cavalli reference, neutralization can be conducted with a 28% sodium hydroxide flow rate, kg/h of 70, a temperature, °C. of 30, and an average residence time, min. of 30. Hydrolysis can be conducted at a temperature, °C. of 160, and an average residence time, min. of 40.

Roberts et al. disclose that internal olefins can be sulfonated in a tubular reactor using $SO_3$ diluted so as to have a concentration of 2.5% in air, the reactor being cooled to between 10° C. and 32° C. In the sulfonation procedure, the olefin flow rate (kg/h) of 16.45, and the $SO_3$/olefin mol ratio is 1.05. One of the clear advantages of the process of the present invention is that conventional batch-type reactors, requiring no special design, can be employed in sulfonating the internal olefins. Prior art workers employing neat internal olefins have generally had to employ falling film reactors or, in any event, specially designed reactors in order to obtain a product of good quality and in high yields. Problems as to specially designed reactors are obviated by the process of the present invention.

In the sulfonation step of the process of the present invention, the solution of the internal olefin in the hydrocarbon solvent is charged to a reactor in the desired amount. Liquid sulfur trioxide is vaporized into a carrier stream, generally heated air, that is passed through the solution of olefin. Generally speaking, the sulfur trioxide is introduced so as to provide a tool ratio of sulfur trioxide to internal olefin of from about 1.0 to 1.0 to about 3.0 to 1.0. In general, the sulfonation temperature is maintained in a range of from about the freezing point of the solvent to about 30° C., preferably to about 10° C.

The intermediate sulfonated compounds present in the reaction mixture are then neutralized, again at a temperature of from about the freezing point of the solvent to about 30° C., with a basic material such as an aqueous solution of an alkali metal hydroxide, ammonium hydroxide, an alkanolamine or other commonly used neutralizing agent. Preferably, the neutralization is carried out with an aqueous alkali metal hydroxide solution such as a sodium hydroxide solution.

To effect hydrolysis, the reaction mixture containing the neutralized, intermediate sulfonated compounds is refluxed at a temperature of from about 100° C. up to about the boiling point of the solvent for a period of time to convert the suitones either to the hydroxy alkane sulfonates or the alkene sulfonates. During hydrolysis, care is taken to maintain the reaction mixture at a pH of about 11 or higher.

Following hydrolysis, the product, primarily a mixture of hydroxy alkane sulfonates and alkene sulfonates, is recovered, typically by adding a hydrophilic liquid, e.g., an alcohol such as isopropanol, to thereby produce two distinct phases. The organic layer is separated and recycled. The aqueous layer is washed twice with a hydrophobic liquid such as hexane, the aqueous layer, neutralized to a pH of about 9, then being evaporated to dryness to recover the product. Optionally, the paraffin and the water from the neutralized and hydrolyzed reaction mixture can be volatilized to yield the sulfonates after adjusting the pH to about 9. It will be appreciated that other methods of recovering the desired product can be employed.

To more fully illustrate the present invention, the following non-limiting examples are presented. In the examples that follow, the following procedures were employed to effect sulfonation of the neat internal olefin and sulfonation of the olefin present in the hydrocarbon solvent.

Typical Neat Olefin Sulfonation (Neat Sulfonation)

To a standard glass batch sulfonation reactor was added 21.8 g (111.2 mmol) 7-tetradecene. Carrier air heated to ~127° C. is passed through the olefin at a rate of 10–11 l/min. Liquid sulfur trioxide, 5 ml (123 mmol), was injected and vaporized into the carrier air at a rate of 0.25 ml/min. The concentration of $SO_3$ in the carrier was thus ~1.25% by volume. The temperature of the olefin is maintained at ~10° C. by applying an isopropanol/dry ice bath intermittently to the reactor. As the reaction proceeded, the mixture turned progressively darker and more viscous. Upon completion of $SO_3$ injection, the dark brown reaction mixture was immediately poured into 71.4 g of a 5.07 wt % aqueous NaOH solution at room temperature with good mixing. Stirring of the yellow emulsion was maintained for about 30 minutes more keeping the pH at about 11 or higher.

The mixture was then refluxed at ~160° C. for about 40 minutes to hydrolyze intermediate sultones. Care was taken to add base when needed throughout the reflux to maintain a pH of 11 or higher. A yellow solid-probably product-formed upon cooling. To separate the surfactant product from residual starting material, hexanes was added to the reaction. To this mixture was introduced isopropanol until all solids were dissolved and two distinct phases were present. The organic layer was separated and discarded. The aqueous layer was washed twice more with fresh aliquots of hexane. The final aqueous layer was neutralized to a pH of ~9 with 3N HCl and evaporated to dryness on a rotary evaporator with repeated addition of isopropanol to control foaming.

The residue was dried under ~25 inches of mercury vacuum at ~70° C. overnight. A brown solid, 24.3 g, is recovered for ~69–73% yield.

Typical Sulfonation of Internal Olefin/Solvent Solution (Dilute Sulfonation)

To a standard glass batch sulfonation reactor was added 32.3 g of a 13 wt % 7-tetradecene in tetradecane mixture (4.20 g, 21.4 mmol 7-tetradecene). Carrier air heated to ~127° C. was passed through the mixture at a rate of 10–11 l/min. Liquid sulfur trioxide 1 ml (24.6 mmol) was injected and vaporized into the carrier air at a rate of 0.25 ml/min. The concentration of $SO_3$ in the carrier was thus ~1.25% by volume. The temperature of the reaction was maintained at ~10° C. by applying an isopropanol/dry ice bath intermittently to the reactor. As the reaction proceeded, the mixture turned progressively darker and slightly more viscous. Upon completion of $SO_3$ injection, the brown reaction mixture was immediately poured into 18.6 g of a 5.19 wt % aqueous NaOH solution at room temperature with good mixing. Stirring of the yellow emulsion was maintained for about 30 minutes more keeping the pH at about 11 or higher.

The mixture was then refluxed at ~160° C. for about 40 minutes to hydrolyze intermediate sultones. Care was taken to add base when needed throughout the reflux to maintain a pH of 11 or higher. A yellow solid–probably product–formed upon cooling. Isopropanol was added to dissolve all solids and produce two distinct layers. The paraffin layer was washed twice with aqueous NaCl and dried over $MgSO_4$. The second layer, the aqueous layer, is washed twice with hexane, neutralized to pH ~9 using 3N HCl, and evaporated to dryness on a rotary evaporator with the addition of isopropanol to control foaming.

The residue recovered was dried under ~25 inches of mercury vacuum at ~70° C. overnight. An orange solid, 5.22 g, was recovered for ~77–82% yield.

For Dilute Sulfonation performed on paraffin diluted olefins, unreacted olefin was estimated by GC analysis of the recovered paraffin layer.

In addition to the sulfonations of 7-tetradecene described above, $C_{13,14}$ internal olefins (IO), neat and dissolved (13% wt) in a $C_{12-16}$ paraffin mixture, were also sulfonated.

Example 1

The table below shows data obtained from the four sulfonation runs.

TABLE 1

|  |  | Estimated % Yield | |
| --- | --- | --- | --- |
|  |  | GC | Prod. Wt. |
| 7-tetradecene | Neat Sulfonation | — | 69–73 |
|  | Dilute Sulfonation | 68 | 77–82 |
| $C^{13,14}$ IO | Neat Sulfonation | — | 73–77 |
|  | Dilute Sulfonation | 91 | 84–89 |

$^1H$ and $^{13}C$ NMR analysis was performed on the samples in the Table. The data in the table shows that higher yields are obtained from Dilute Sulfonation. Moreover, it was found that products prepared from Dilute Sulfonation were at least equal to the quality of those prepared from Neat Sulfonation. This is of significant economic value since it enables the internal olefin sulfonates to be prepared from readily available streams without the necessity for prior separation of the internal olefins from other components.

Example 2

Using the sulfonation procedures set out above, sulfonation experiments were run in triplicate to compare products obtained from Dilute Sulfonation with products obtained from Neat Sulfonation. In all cases, the internal olefins were $C_{13,14}$ internal olefins, either neat or as a 13% solution in a $C_{12-16}$ paraffin mixture.

For each set of experiments, proton NMR spectra were obtained on the products in an attempt to determine if there were differences in the types of sulfonated products produced. In all cases it was found that significantly more alkene sulfonates were produced by Dilute Sulfonation than by Neat Sulfonation. This is important since it demonstrates that by using the process of the present invention wherein the internal olefin is diluted in an inert hydrocarbon solvent, the alkene sulfonate level of the produced product can be increased.

Surfactant studies on the sulfonated internal olefins produced according to the process of the present invention confirm that they possess detergency characteristics comparable to linear alkyl benzene sulfonates.

The foregoing description and examples illustrate selected embodiments of the present invention. In light thereof, variations and modifications will be suggested to one skilled in the art, all of which are in the spirit and purview of this invention.

What is claimed is:

1. A process for sulfonating internal olefins comprising:

sulfonating a solution of internal olefins having the general formula:

$$R_1\text{---CH}\!=\!\text{CH---}R_2$$

wherein $R_1$ and $R_2$ may be the same or different and are each an alkyl group containing from about 1 to about 30 carbon atoms with a sulfonating agent in a hydrocarbon solvent that is substantially inert under sulfonation conditions and does not deleteriously affect sulfonation of said internal olefins to produce a reaction mixture containing intermediate sulfonated compounds, said internal olefins being present in said solvent in an amount of from about 5 to about 40% by weight;

neutralizing said intermediate sulfonated compounds in said reaction mixture under conditions to form neutralized sulfonated compounds;

hydrolyzing said neutralized sulfonated compounds in said reaction mixture under conditions to form a product mixture containing hydroxy alkane sulfonates and alkene sulfonates; and recovering said product mixture from said solution.

2. The process of claim 1 wherein said internal olefins are present in said solution in an amount of from about 8 to about 15% by weight.

3. The process of claim 1 wherein said sulfonation is conducted using gaseous sulfur trioxide as a sulfonating agent.

4. The process of claim 1 wherein said neutralization is conducted using an alkali metal hydroxide solution.

5. The process of claim 1 wherein said hydrocarbon solution comprises a mixture of paraffinic hydrocarbons.

6. The process of claim 1 wherein said sulfonating is conducted at a temperature in the range of from about the freezing point of said solvent to about 30° C.

7. The process of claim 1 wherein said neutralizing is conducted at a temperature in the range of from about the freezing point of said solvent to about 30° C.

8. The process of claim 1 wherein said hydrolysis is conducted at a temperature of from about 100° C. to about the boiling point of said solvent.

9. The process of claim 1 wherein $R_1$ and $R_2$ are alkyl groups, each of $R_1$ and $R_2$ containing from about 4 to about 15 carbon atoms.

\* \* \* \* \*